(12) United States Patent
Heil, Jr.

(10) Patent No.: US 7,496,410 B2
(45) Date of Patent: Feb. 24, 2009

(54) SPRING FIXATION MECHANISM FOR EPICARDIAL LEADS

(75) Inventor: Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 553 days.

(21) Appl. No.: 11/032,445

(22) Filed: Jan. 10, 2005

(65) Prior Publication Data

US 2006/0155353 A1 Jul. 13, 2006

(51) Int. Cl.
*A61N 1/00* (2006.01)
(52) U.S. Cl. .................................................. 607/126
(58) Field of Classification Search ................ 607/116, 607/119, 126, 127, 122; 600/375, 374, 373
See application file for complete search history.

(56) References Cited

U.S. PATENT DOCUMENTS

| | | | | |
|---|---|---|---|---|
| 5,003,992 A | * | 4/1991 | Holleman et al. ............ 607/120 |
| 5,020,545 A | * | 6/1991 | Soukup ....................... 607/127 |
| 5,347,708 A | * | 9/1994 | Bischoff et al. .............. 29/825 |
| 5,545,206 A | * | 8/1996 | Carson ........................ 607/126 |
| 5,575,814 A | * | 11/1996 | Giele et al. .................. 607/127 |
| 5,697,936 A | * | 12/1997 | Shipko et al. ................ 606/108 |
| 5,759,202 A | * | 6/1998 | Schroeppel .................. 607/126 |
| 6,687,550 B1 | | 2/2004 | Doan |
| 2004/0015193 A1 | * | 1/2004 | Lamson et al. ............... 607/9 |
| 2004/0059404 A1 | * | 3/2004 | Bjorklund et al. ........... 607/126 |
| 2004/0116992 A1 | | 6/2004 | Wardle et al. |

FOREIGN PATENT DOCUMENTS

WO WO 03/092801 A1 11/2003

* cited by examiner

*Primary Examiner*—Mark W Bockelman
*Assistant Examiner*—Roland Dinga
(74) *Attorney, Agent, or Firm*—Faegre & Benson LLP

(57) ABSTRACT

A spring fixation mechanism is adapted for fixing the distal end of an epicardial lead in a myocardium of the heart. The spring fixation mechanism is positioned at a distal end of the lead and includes a spring member and a stop. The spring member is formed about the lead and extends from a proximal end slidable relative to the lead to a distal end fixed to the lead. The stop is coupled to the proximal end of the spring member and is sized to be retained outside of an epicardium of the heart. The distal end of the lead, including the spring fixation mechanism, is inserted into the myocardium with a stylet and/or a pusher tube. The spring member is loaded and released, grasping tissue between adjacent coils of the spring member, fixing the lead within the myocardium.

23 Claims, 7 Drawing Sheets

SPRING FIXATION MECHANISM FOR EPICARDIAL LEADS

TECHNICAL FIELD

The present invention is directed toward leads for sensing and/or stimulating electrical signals in muscle tissue. More specifically, it is directed toward fixation of such leads to the epicardium.

BACKGROUND

Implantable medical devices for treating heart arrhythmias with electrical stimuli are well known in the art. Some of the most common forms of such implantable devices are defibrillators and pacemakers. Various types of lead and electrode assemblies for defibrillators and pacemakers have been suggested in the prior art. One type of cardiac lead is the epicardial lead, which is either attached to the outer layer of the heart, the epicardium, or is embedded in myocardium (muscle) after penetrating the epicardium.

For optimal chronic performance of an implantable lead, stable attachment of the electrode to the targeted tissue is required. Currently, attachment of epicardial leads is typically accomplished through the use of sutures, screws, hooks, barbs, and other such devices. These devices present significant attachment challenges. For example, these devices often require a considerable incision to access the heart during implantation. Furthermore, forces generated between the device and tissue are highly dependent on surgical technique, and thus are often not uniform.

There exists a need for improved devices for epicardial attachment of electrical leads. There is a further need for such devices that are compatible with minimally invasive surgical methods.

SUMMARY

According to one embodiment, the present invention is a lead for insertion into a myocardium of a heart. The lead includes a lead body, an electrode and a spring fixation mechanism. The lead body has a proximal end, a distal end, and one or more conductors disposed therein. The electrode is coupled near the distal end of the lead body. The spring fixation mechanism includes a spring member and a stop. The spring member is formed about the lead body and extends from a spring proximal end slidable relative to the lead body to a spring distal end fixed to the lead body. The stop is coupled to the spring proximal end and is sized to be retained outside of an epicardium of the heart.

According to still another embodiment, the present invention is a cardiac rhythm management system. The system includes a pulse generator, a lead body, an electrode, and a spring fixation means for fixing a distal end of the lead in the myocardium. The lead body has a proximal end coupled to the pulse generator, the distal end, and one or more conductors disposed therein. The electrode is near the distal end of the lead body.

According to yet another embodiment, the present invention is a method for implanting a lead into a myocardium of the heart. A spring member is provided about a distal end of the lead, and has a distal end fixed to the lead and a proximal end slidable relative to the lead. The distal end of the lead is inserted into the myocardium. A portion of the spring member positioned in the myocardium is loaded and then released such that adjacent coils of the spring member trap tissue of the myocardium.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
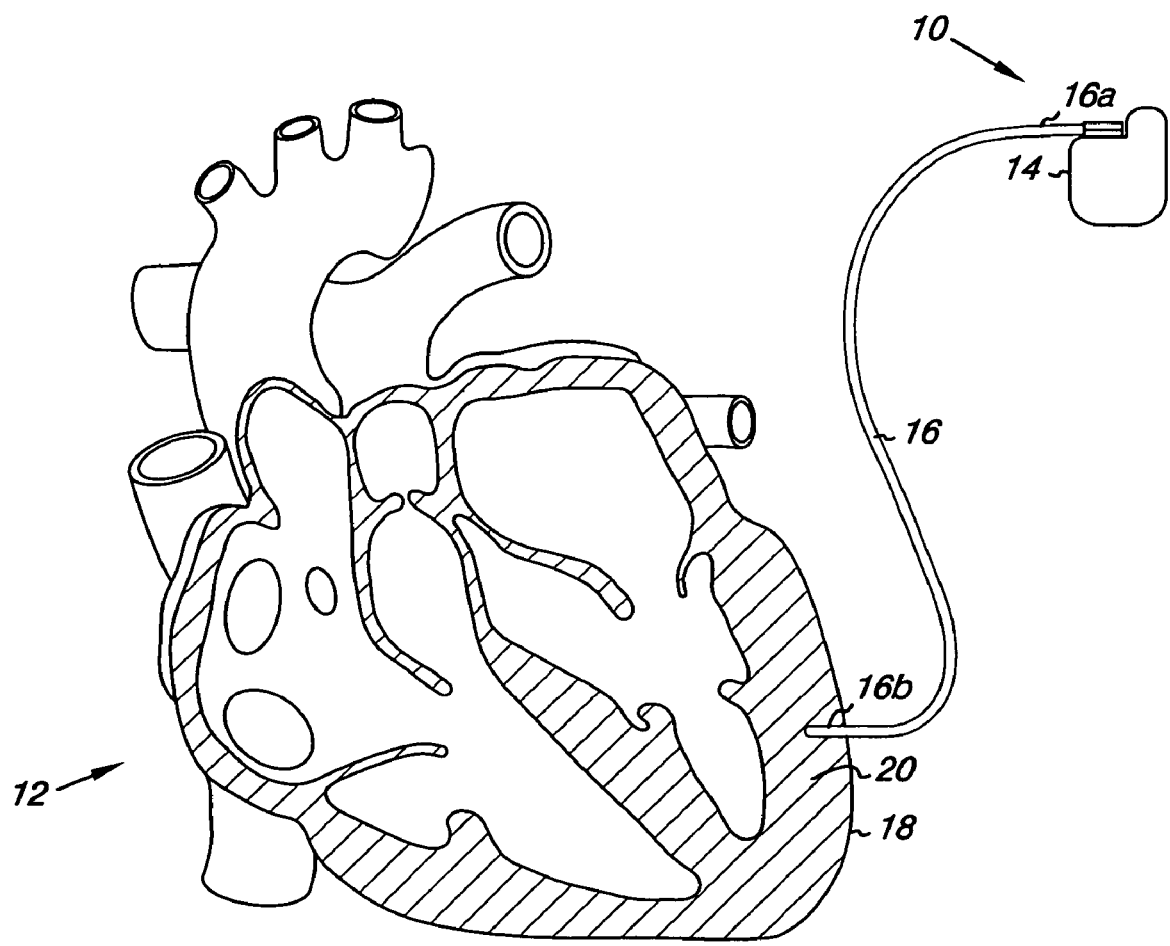
FIG. 1 is a schematic view showing a cardiac rhythm management system according to one embodiment of the present invention in relation to a heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view showing a cardiac rhythm management ("CRM") system 10 according to one embodiment of the present invention in relation to a heart 12. The CRM system 10 includes a pulse generator 14 coupled to an epicardial lead 16. The lead 16 extends from a proximal end 16a coupled to the pulse generator 14 to a distal end 16b that passes through an epicardium 18 of the heart 12 and is implanted in the myocardium 20. The present invention, in one embodiment, is a lead attachment system relating to the anchoring or fixation of the lead 16 to the heart 12.

Figure 2:
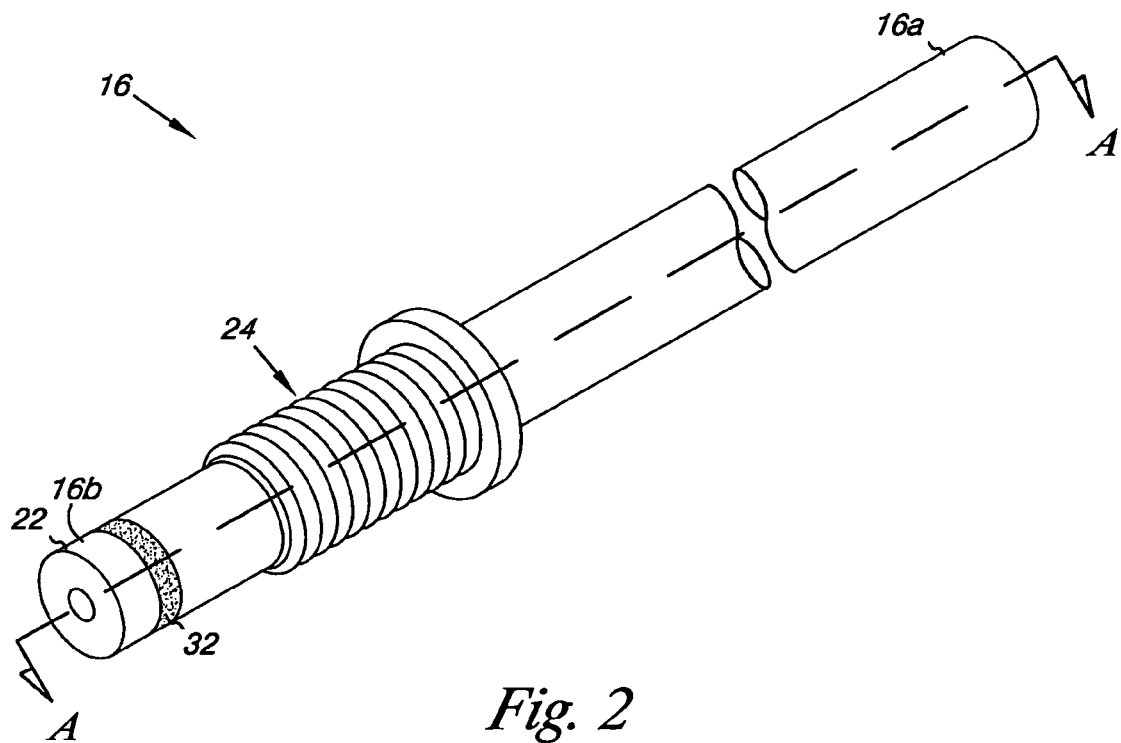
FIG. 2 is a perspective view of a distal portion of a lead in accordance with one embodiment of the present invention.

FIG. 2 is a perspective view of the distal end 16b of the lead 16. As shown in FIG. 2, the lead 16 includes a pacing electrode 22 and a spring fixation mechanism 24 for facilitating anchoring or fixation of the lead 16 in the heart 12.

Figure 3:
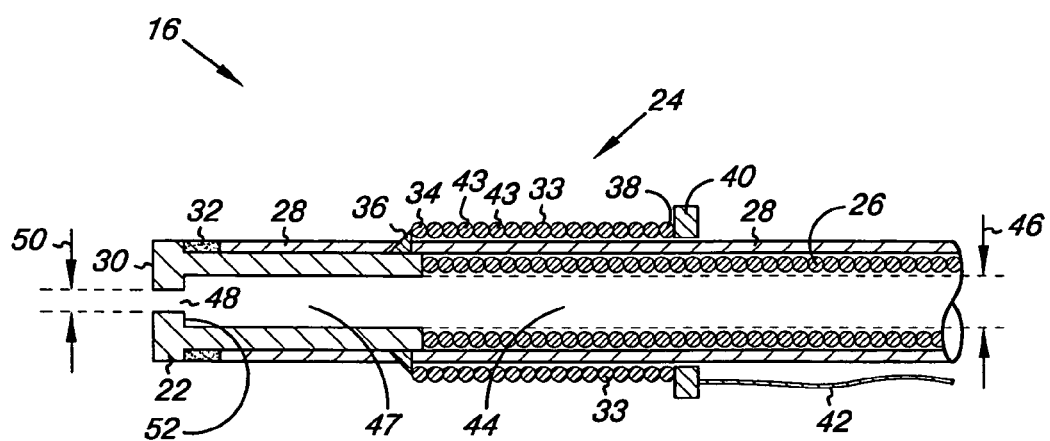
FIG. 3 is a cross-sectional view of the lead of FIG. 2 taken along line A-A.

FIG. 3 is a cross-sectional view of a portion of the lead 16 of FIG. 2 taken along line A-A. As shown in FIG. 3, a coil conductor 26 runs the length of the lead 16 and is welded or otherwise electrically coupled to the pacing electrode 22. An insulator 28 sheaths the coil conductor 26 and pacing electrode 22 except at a distal tip 30 of the lead 16. In one embodiment, the electrode 22 includes a drug collar 32 that can release steroids or other agents after implantation to enhance efficacy of the electrode 22 or to promote healing of the heart 12.

The spring fixation mechanism 24 includes a spring member 33 having a distal end 34 connected to an attachment ring 36 that is, in turn, connected to the sheath 28 near the pacing electrode 22. Alternately, the attachment ring 36 is connected to the electrode 22, the coil conductor 26 or another component (not shown) that would provide a less flexible bond to the lead 16 than the sheath 28.

The spring member 33 extends proximally from the attachment ring 36 and surrounds the lead 16. A proximal end 38 of the spring member 33 is not attached to the lead 16, but is rather free to slide relative to the lead 16, as are all portions of the spring member 33 except the anchored distal end 34. A stop ring 40 is attached to the proximal end 38 of the spring member 33. The stop ring 40 is an enlarged or deployable component having a notably greater outer diameter than an outer diameter of the spring member 33. In fact, although shown as ring-shaped, such a component may have other configurations adapted to function as a stop retained outside of the epicardium 18. In some embodiments, a cord 42 is attached to the stop ring 40 and extends proximally. As further explained below, the cord 42 may be used to apply tension to the stop ring 40 and extend the spring member 33.

The distal end 34 of the spring member 33 is spaced from the distal tip 30 of the lead 16 an appropriate distance depending on the desired location of the electrode 22 in the myocardium 20. In one embodiment, the distal end 34 of the spring member 33 is spaced apart from the distal tip 30 of the lead 16 by approximately 1 cm. This spacing, however, can be increased or decreased to accommodate a heart 12 exhibiting unusual or diseased physiology, which may cause the epicardium 18 and/or myocardium 20 to be thicker or thinner than normal. In addition, the attachment ring 36 may be connected to the sheath 28 or the distal end 34 of the spring member 33 may be directly connected to the lead 16 without the attachment ring 36.

The spring member 33 is an extension-type coil spring adapted to lengthen proportionally to a longitudinally applied, or loading, force. In some embodiments, as shown in FIG. 3, the spring member 33 is a close-wound extension spring, in which adjacent coils 43 are in contact in the absence of an external loading force. In alternate embodiments, adjacent coils 43 are slightly spaced apart in the absence of an external loading force (not shown). The spring member 33, in one embodiment, has a length of from about 5 mm to about 10 mm in the absence of a loading force (i.e., when relaxed). The spring member 33, in one embodiment, has a spring pitch of from about 150 to about 200 coil turns per inch. In another embodiment, the spring member 33 has a coil pitch approximately equal to that of the coil conductor 26. Finally, in one embodiment, the spring member 33 has a spring rate, or resistance to a loading force, sufficient to resist at least about 100 grams of tension.

In one embodiment, the spring member 33 is formed from a coiled wire having a smooth circular cross-section, as shown in FIG. 3. In another embodiment, the spring member 33 includes surface texturization. According to yet another embodiment, the spring member 33 is formed or enmeshed with dacron or another fabric-like material adapted to promote tissue grasping and chronic tissue ingrowth. According to still other embodiments, the spring member 33 is formed from a coiled member having a non-circular cross section (not shown).

FIG. 3 further shows the interior arrangement of the lead 16 according to one embodiment of the present invention. Along the length of the lead 16, the coil conductor 26 defines a lumen 44 having a lumen diameter 46. The conductor lumen 44 is continuous with an electrode lumen 47 extending through the pacing electrode 22. An opening 48 from the electrode lumen 47 is provided at the distal tip 30 of the lead 16. The opening 48 has an opening diameter 50 that has a smaller magnitude than that of the conductor lumen diameter 46. Internal to the pacing electrode 22, at the transition from the electrode lumen 47 to the opening 48, there is an internal stop 52.

Figure 4:
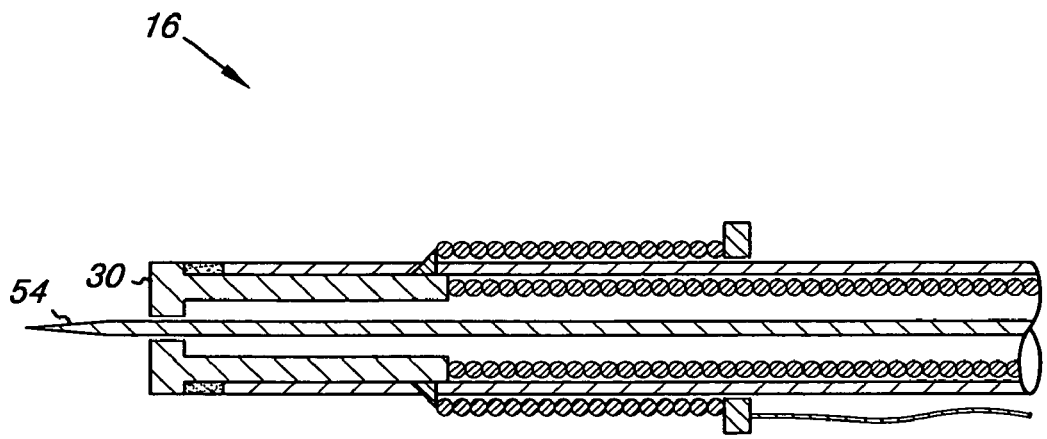
FIG. 4 is a cross-sectional view of the lead of FIG. 2 taken along line A-A and assembled with a stylet.
Figure 5:
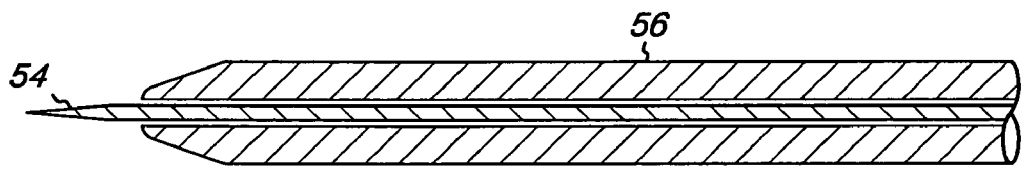
FIG. 5 is a cross-sectional view of the stylet of FIG. 4 assembled with a dilator.
Figure 6:
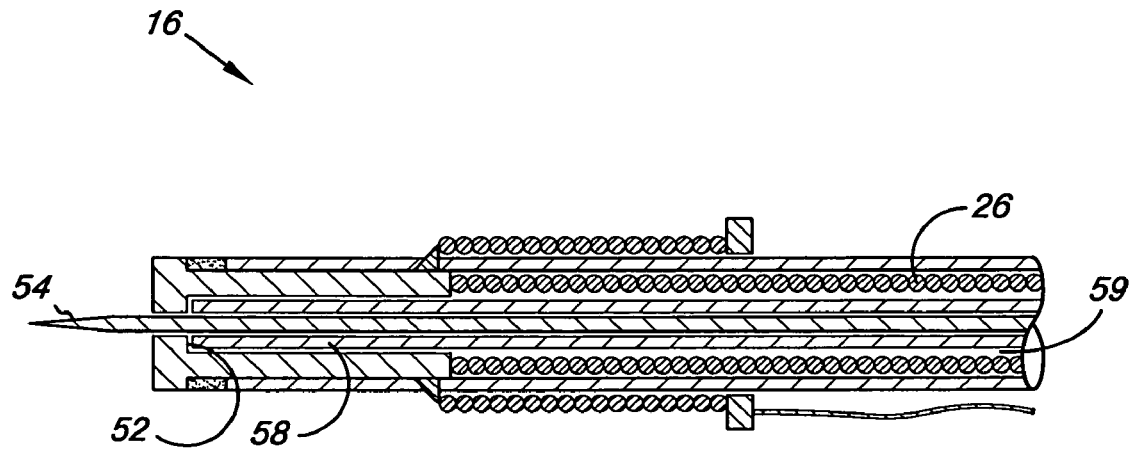
FIG. 6 is a cross-sectional view of the lead of FIG. 2 taken along line A-A and assembled with a stylet and a pusher tube.

In some embodiments, the lead attachment system includes a stylet 54 dimensioned to be received in the lumen 44 such that the lead 16 may slide freely over it, as shown in FIG. 4. As shown, the stylet 54 may be advanced beyond the distal tip 30 of the lead 16 to form a passageway to the heart 12 to facilitate insertion of the lead 16 into the heart 12. A dilator 56, as shown in FIG. 5, may be inserted over the stylet 54 prior to the lead 16 to expand the size of the passageway into the heart 12 formed by the stylet 54 alone. Still other embodiments may include a pusher tube 58, as represented in FIG. 6, dimensioned to slide in an annular space 59 defined in the conductor lumen 44 between the stylet 54 and the lead 16. The pusher tube 58 is inserted into the annular space 59 and bears on the internal stop 52 to drive the lead 16 into the heart 12. Some embodiments include combinations of a stylet 54, a dilator 56, and a pusher tube 58.

Figure 7:
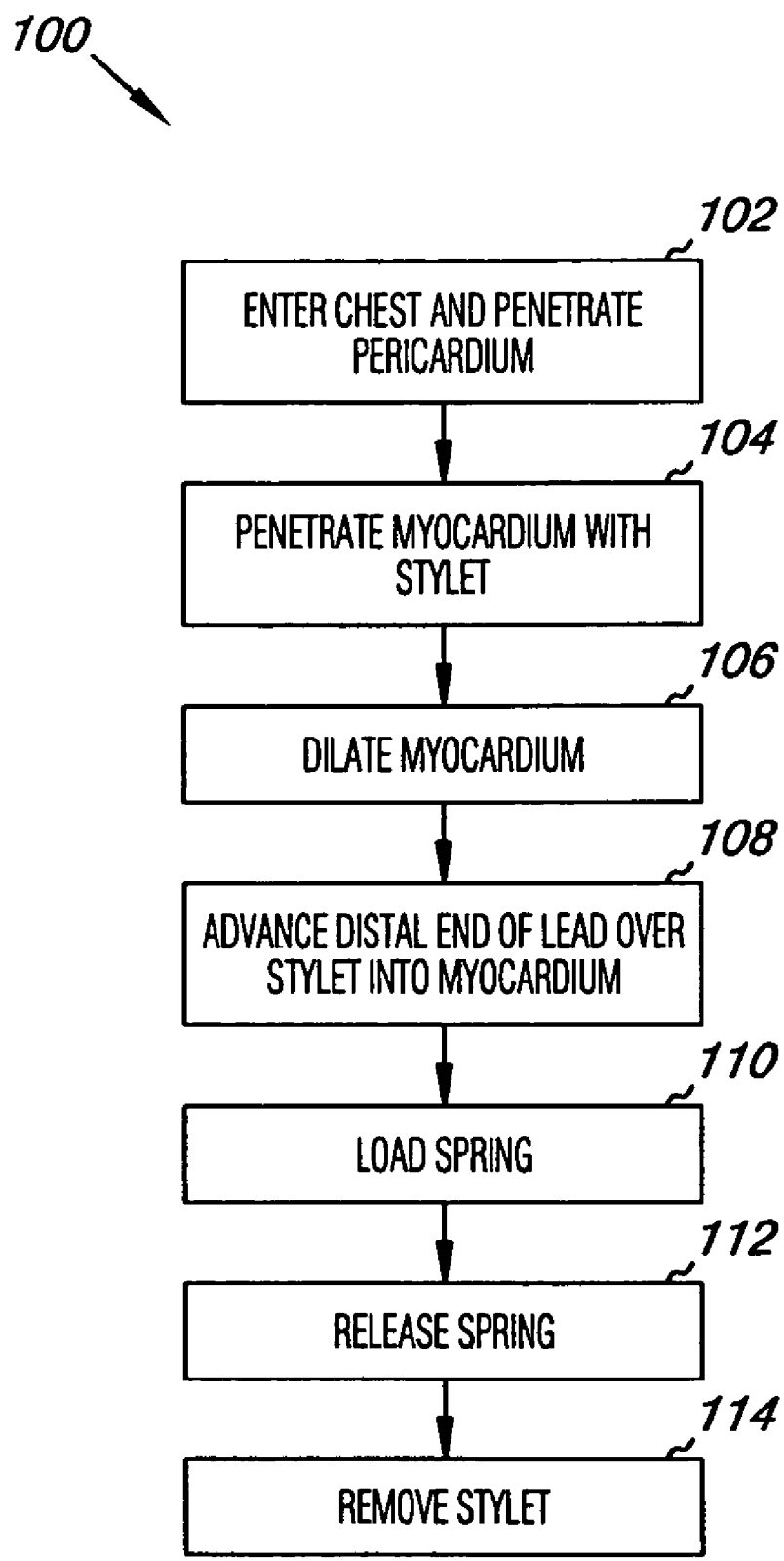
FIG. 7 is a flowchart showing a method 100 of attaching a lead to an epicardium, according to one embodiment of the present invention.

FIG. 7 is a flowchart summarizing a method 100 for implanting a lead according to one embodiment of the present invention. Any minimally-invasive technique is used to enter the patient's chest and penetrate the pericardium of the heart 12 as is known in the art (block 102). Possible epicardial approaches include, for example, thoracic and subxiphoid approaches. A stylet 54 is brought to the epicardial surface at the desired implantation location and advanced through the epicardium 18 into the myocardium 20, forming a channel (block 104). A dilator 56 is passed over the stylet 54 into the myocardium 20 to increase the diameter of the channel formed, then withdrawn (block 106).

The distal end 16b of the lead 16 is advanced over the stylet 54 into the myocardium 20 (block 108). The force necessary for advancing the distal end 16b of the lead 16 into the myocardium 20 can be provided by a physician pushing on the lead 16 at its proximal end 16a. Because epicardial leads are generally flexible, and may not have the rigidity necessary to transmit a longitudinally applied force from the proximal end 16a to the distal end 16b, the pusher tube 58 is employed to exert force on the distal end 16b of the lead 16. The pusher tube 58 is inserted into the annular space 59 and advanced to bear on the internal stop 52. In this manner, the distal end 16b of the lead 16 is advanced into the myocardium 20.

As the physician advances the distal end 16b of the lead 16, including the pacing electrode 22, through the epicardium 18 and into the myocardium 20, the stop ring 40, because of its enlarged outer diameter, is retained outside of the epicardium 18. As the distal end 34 of the spring member 33 continues to advance through the myocardium 20, the spring member 33 becomes loaded (block 110). Loading the spring member 33 causes the spring member 33 to elongate, opening intra-coil gaps 60 (See FIG. 8). As the distal end 34 of the loaded spring member 33 is advanced through the myocardium 20, the "clicking" progression of successive coil turns 43 passing through the relatively tough epicardium 18 provides tactile feedback, helping the physician to gauge the depth of the lead's distal tip 30 within the myocardium 20.

The physician reduces or eliminates the force applied to the lead 16 or pusher tube 58, releasing the spring member 33

(block 112). Releasing the spring member 33 allows the spring member 33 to contract, grasping tissue caught in the intra-coil gaps 60. In one embodiment, tissue of both the epicardium 18 and myocardium 20 are fixed by the spring member 33, with the tougher epicardial tissue providing the more secure grip. For chronic lead placement, fibrotic (scar) tissue ingrowth around the spring coils 43 may provide additional fixation. After the lead 16 is secure, the stylet 54 and/or pusher tube 58 are removed (block 114).

Figure 8:
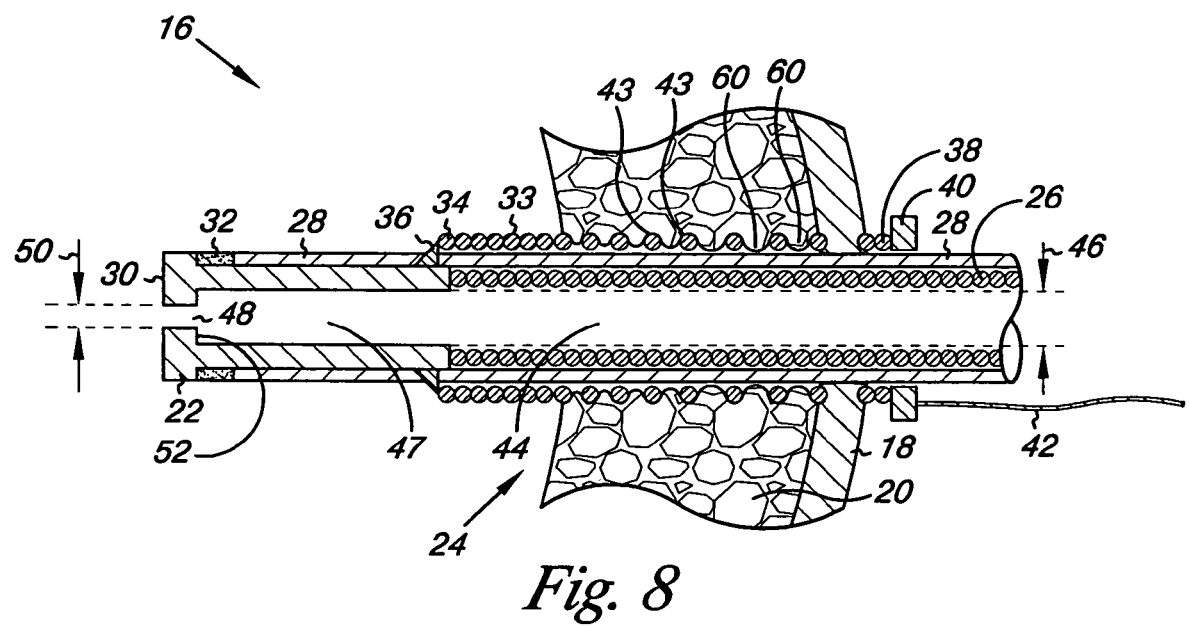
FIG. 8 is a cross-sectional view showing the lead of FIG. 2 implanted in the myocardium and epicardium of the heart.

FIG. 8 shows the lead 16 fixed in place after the implantation is completed, according to one embodiment of the present invention. As is shown in FIG. 8, tissue of both the epicardium 18 and the myocardium 20 are grasped between adjacent coils 43.

Those embodiments including a biocompatible cord 42 attached to the stop ring 40 are deployed in a method similar to the method 100 represented in FIG. 7. However, as the distal end 16b of the lead 16 is advanced into the myocardium 20, tension is applied to the cord 42 to contribute to the loading and elongation of the spring member 33. The use of the cord 42 makes it possible to load or stretch the spring member 33 while applying less or no compression to the epicardium 18, potentially reducing trauma. After implantation, the cord 42 remains in the body inertly, or, in the case of a biodegradable cord 42, degrades over time. Should removal of the lead 16 be required, tension on the cord 42 in combination with force directed distally via the lead body 26 or pusher tube 58 can elongate the spring member 33 and release the tissue from the intra-coil gaps 60, reversing fixation.

Fixation may also be reversed by rotating the lead 16. The helical turns of the spring member 33 act like "threads," guiding the distal end 16b of the lead 16 as it backs out or "unscrews" from the myocardium 20 and epicardium 18.

In some embodiments, there is no dilation step (block 106), but rather, the lead 16 is advanced (block 108) directly following the penetration by the stylet 54 (block 104). In another embodiment, the lead 16 and stylet 54 are slidably assembled prior to implantation, and simultaneously advanced into the heart 12. In yet another embodiment, the lead 16, stylet 54, and pusher tube 58 are pre-assembled and simultaneously advanced into the heart 12. The spring member 33 may be loaded or stretched by tensioning the cord 42 prior to, during, or after insertion of the lead 18 into the myocardium 20.

The lead 16 is optionally provided with a second pacing electrode proximal to electrode 22 to enable bipolar sensing and pacing (not shown). The proximal electrode may be positioned either proximal or distal to the spring member 33, depending upon where the physician chooses to target tissue for stimulation. According to another embodiment, the second electrode is positioned on the lead 16 underneath the spring member 33. Tissue trapped in the intra-coil gaps 60 contacts the second electrode, providing a stable site for both sensing and pacing. According to still another embodiment, the spring member 33 itself is electrically coupled to the pulse generator 14. In this manner, the spring member 33 acts as a second electrode.

Figure 9A:
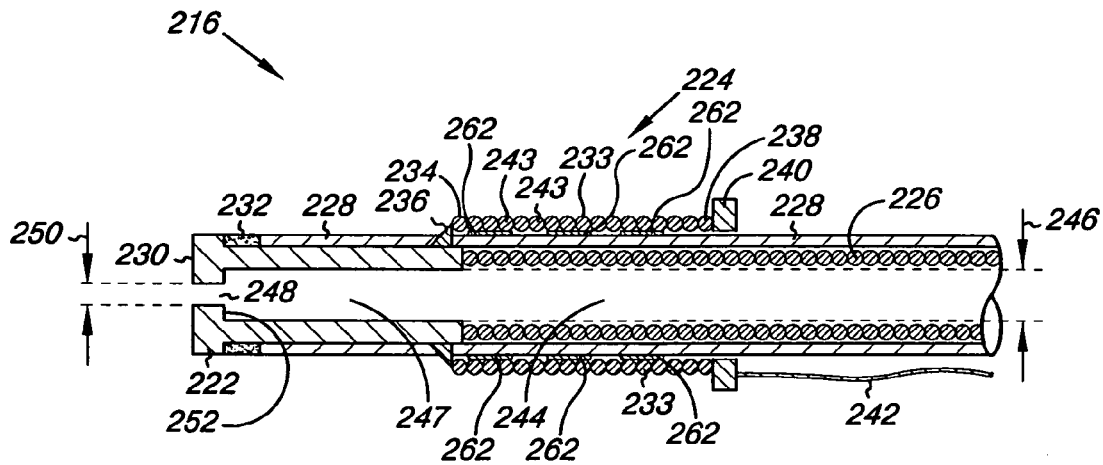
FIG. 9A is a cross-sectional view of a lead according to another embodiment of the present invention.
Figure 9B:
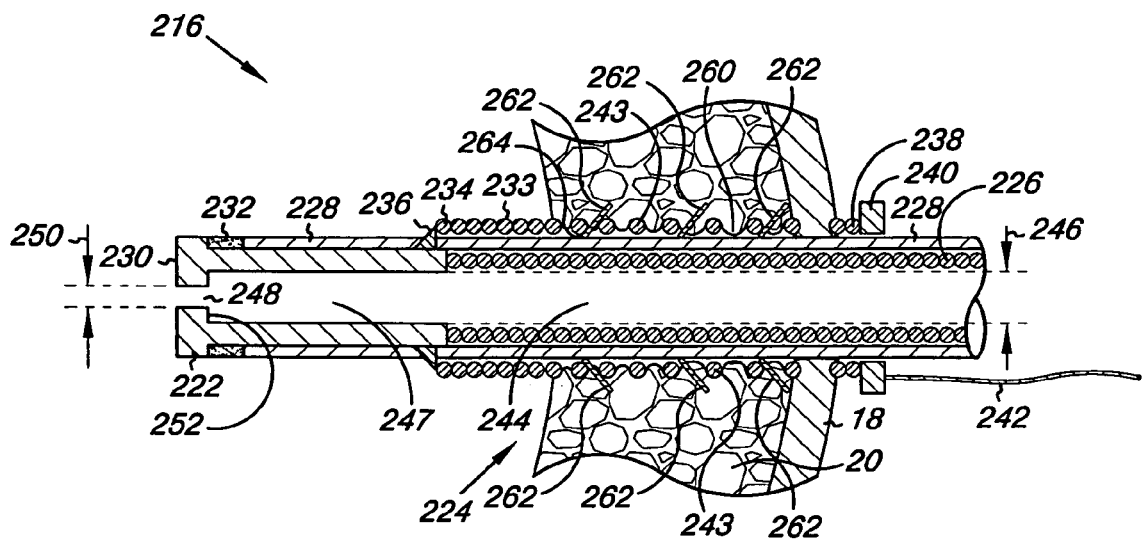
FIG. 9B is a cross-sectional view of the lead of FIG. 9A in a deployed configuration.

FIGS. 9A and 9B show an epicardial lead 216 according to another embodiment of the present invention. The lead 216 is similar to the embodiments shown generally in FIGS. 2 and 3, and like parts are given like numbering. The lead 216 includes an electrode 222 at a distal end 216b, and is provided with a spring fixation mechanism 224 for fixing the lead 216 in the myocardium 20. The spring fixation mechanism 224 of the present embodiment further includes at least one tine member 262 coupled to the lead 216 and positioned underneath the spring member 233. The tine member 262 extends along a longitudinal axis of the lead 216 and is pivotably coupled to the lead 216 at a distal end 264.

The tine member 262 is retained in a flattened configuration, against the lead 216, by the unloaded spring member 233. Upon loading of the spring member 233 during insertion into the myocardium 20, as previously described, the coils 243 of the spring member 233 become spaced apart, creating intra-coil gaps 260. When the intra-coil gap 260 adjacent the tine member 262 is sufficiently large, the tine member 260 is released from its flattened position and pivots outwardly into the adjacent gap 260. As shown in FIG. 9B, the deployed tine member 262 engages the tissue of the myocardium 20 and/or the epicardium 18, resisting proximal sliding of the lead 216. The tine member 262 provides lead fixation in addition to the pinching action when tissue is grasped between adjacent coils 243. According to one embodiment, the lead 216 is provided with a plurality of tine members 262 disposed about the lead circumference.

According to one embodiment, the tine member 262 is biased to a deployed position. According to another embodiment, the tine member 262 is coupled to the spring member 233, such that upon loading and stretching of the spring member 233, the tine member 262 is drawn upwardly as the spring member 233 elongates.

Figure 10A:
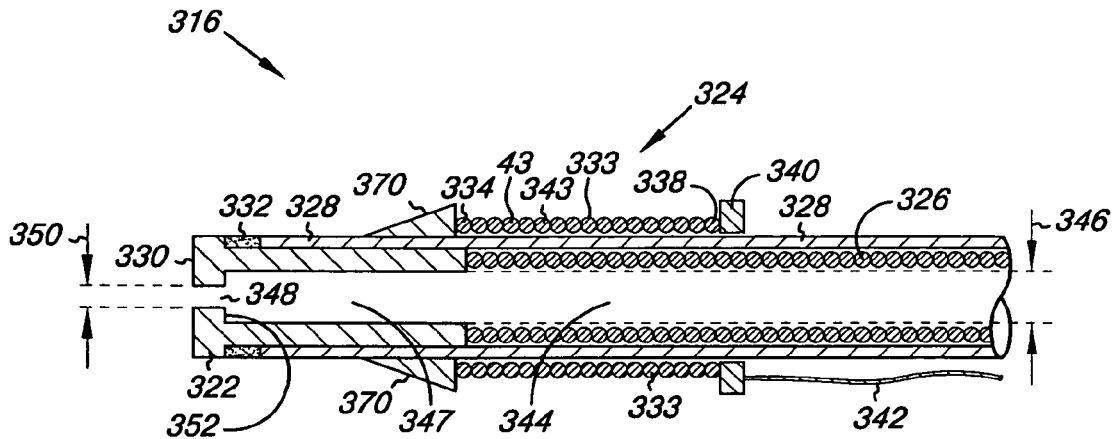
FIG. 10A is a cross-sectional view of a lead according to another embodiment of the present invention.
Figure 10B:
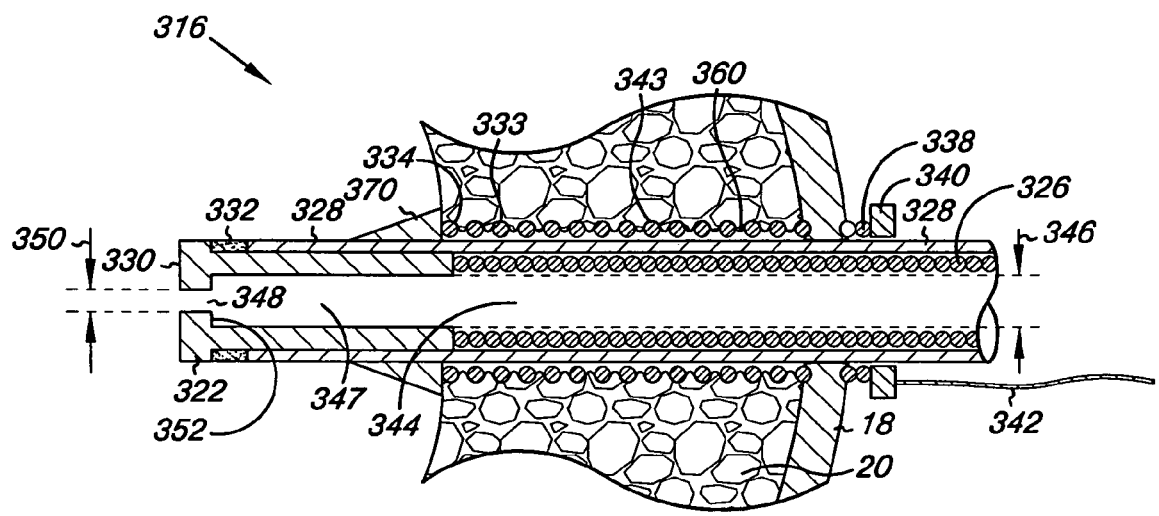
FIG. 10B is a cross-sectional view of the lead of FIG. 10A in a deployed configuration.

FIGS. 10A and 10B show an epicardial lead 316 according to another embodiment of the present invention. The lead 316 is similar to the embodiment shown generally in FIGS. 2-8, and like parts are given like numbering. As shown in FIG. 10A, the lead 316 includes a distal electrode 322 and a spring fixation mechanism 324. The spring fixation mechanism 324 includes a spring member 333 connected at a distal end 334 to the electrode 322 and coupled to a slidable stop ring 340 at a proximal end 338. The spring fixation mechanism 324 further includes a wedge-shaped member 370 formed about at least a portion of the lead 316 at the distal end 334 of the spring member 333.

The lead 316 is inserted into the myocardium 20 as discussed previously. As is shown in FIG. 10B, the wedge 370 advances beyond the epicardium 18 and into the myocardium 20, but the stop ring 340 does not. Thus, the stop ring 340 bears down on the epicardium 18 and is retained on an outer surface of the epicardium 18. As the lead 316 is advanced further through the myocardium 20, the spring member 333 becomes loaded and stretches. Upon release of the driving force the spring member 333 retracts. Doing so causes the stop ring 340 and wedge 370 to be drawn together by the spring force. The epicardium 18 and myocardium 20 are pinched between the stop ring 340 and the wedge 370. The pinching action between the stop ring 340 and wedge 370 provides a fixation force in addition to the grasping of tissue between adjacent coils 343.

According to another embodiment, the wedge 370 is advanced just beyond the epicardium 18. Upon release of the spring member 333, the epicardium 18 is pinched between the wedge 370 and the stop ring 340. According to one embodiment, the distal wedge 370 is driven through to the surface of the endocardium (not shown). Upon release, the spring fixation mechanism 324 pinches together the endocardium and the epicardium 18, with the myocardium 20 sandwiched between the two. The electrode 322 should be electrically coupled to the wedge 370 so as to maintain suitable contact with the myocardium 20. Alternately, the electrode 322 should extend proximally relative to the wedge 370 so as to remain inserted in the myocardium 20 even when the wedge 370 is positioned at the endocardium (not shown).

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

I claim:

1. A lead for insertion into a myocardium of a heart, the lead comprising:
    a lead body defining a lumen extending therethrough, the lead body having a proximal end, a distal end and one or more conductors disposed therein, the lead body distal end having an exit port for the lumen;
    a stylet slidably disposed in the lumen and having a sharpened distal end, the stylet having a size and length sufficient to pass through the lumen and exit the lumen through the distal port such that the sharpened distal end can be extended from the lead body distal end to pierce the myocardium, providing a pilot hole for the lead body;
    an electrode coupled near the distal end of the lead body; and
    a spring fixation mechanism including a spring member and a stop, the spring member formed about the lead body and extending from a spring proximal end slidable relative to the lead body to a spring distal end fixed to the lead body, the stop coupled to the spring proximal end and sized to be retained outside of an epicardium of the heart such that as the lead body is advanced into the epicardium using a distally directed axial force, the spring is stretched between the stop and the distal end of the spring, and, upon removal of the axial force, the spring retracts, capturing epicardial tissue between coils of the spring.

2. The lead of claim 1 further comprising a dilator slidably received over the stylet.

3. The lead of claim 1 further comprising a rigid tube slidably received in the lumen, and wherein a distal end of the lumen is formed with an internal stop for transmitting a longitudinally directed force from the tube to the distal end of the lead.

4. The lead of claim 1 further comprising a tensioning member having a distal end coupled to the stop and extending proximally therefrom.

5. The lead of claim 4 wherein the tensioning member is formed from either of a biodegradable or bioabsorbable material.

6. The lead of claim 4, wherein the tensioning member is a cord.

7. The lead of claim 1 wherein the spring fixation mechanism further comprises an attachment ring coupling the spring distal end to the lead body.

8. The lead of claim 1 wherein the spring member is a close-wound extension coil spring.

9. The lead of claim 1 wherein the spring member is provided with a texturized outer surface.

10. The lead of claim 1 wherein the spring member is provided with an outer surface adapted to promote tissue ingrowth.

11. The lead of claim 1 wherein the spring member is a second electrode.

12. The lead of claim 1 wherein the spring member has a length of from about 5 mm to about 10 mm.

13. The lead of claim 1 further comprising a drug collar positioned on the distal end of the lead body.

14. The lead of claim 1 wherein the spring fixation mechanism further comprises at least one tine member pivotably coupled to the lead and deployable from a collapsed configuration to a protruding configuration upon elongation of the spring member.

15. The lead of claim 1 wherein the spring fixation mechanism further includes a wedge-shaped member positioned on the lead distal to the stop, the wedge-shaped member having a smaller end facing distally and a larger end facing proximally.

16. A lead for insertion through an epicardium and into a myocardium of a heart, the lead comprising:
    a lead body defining a lumen extending therethrough, the lead body having a proximal end, a distal end and one or more conductors disposed therein, the lead body distal end having an exit port for the lumen;
    a stylet slidably disposed in the lumen and having a sharpened distal end, the stylet having a size and length sufficient to pass through the lumen and exit the lumen through the distal port such that the sharpened distal end can be extended from the lead body distal end to pierce the myocardium, providing a pilot hole for the lead body;
    an electrode coupled near the distal end of the lead body;
    a spring fixation mechanism including a spring member and a stop, the spring member formed about the lead body and extending from a spring proximal end to a spring distal end fixed to the lead body, the spring proximal end slidable relative to the lead body such that the lead body can be held immobile while the proximal end is slid along the lead body, the stop coupled to the spring proximal end and sized to be retained outside of an epicardium of the heart, wherein the stop has a first position along the lead body corresponding to a contracted configuration of the spring and a second position along the lead body corresponding to an extended configuration of the spring, the first position being distal of the second position; and
    a tensioning member having a distal end coupled to the stop and extending proximally therefrom, the tensioning member slidable relative to the lead body such that placing tension on the tensioning member while holding the lead body immobile causes the proximal end of the spring member to be moved proximally along the lead body, stretching the spring member.

17. The lead of claim 16 wherein adjacent windings of the spring are abutting one another in the contracted configuration.

18. The lead of claim 16 wherein adjacent windings of the spring are spaced apart from one another in the contracted configuration.

19. The lead of claim 16 further comprising a rigid tube slidably received in the lumen, and wherein a distal end of the lumen is formed with an internal stop for transmitting a longitudinally directed force from the tube to the distal end of the lead.

20. The lead of claim 16 wherein the spring fixation mechanism further comprises at least one tine member pivotably coupled to the lead and deployable from a collapsed configuration to a protruding configuration upon elongation of the spring member.

21. The lead of claim 16 wherein the spring fixation mechanism further includes a wedge-shaped member positioned on the lead distal to the stop, the wedge-shaped member having a smaller end facing distally and a larger end facing proximally.

22. The lead of claim 16 wherein the spring member is a second electrode.

23. The lead of claim 16, wherein the tensioning member is a cord.

* * * * *